US00PP25695P3

(12) United States Plant Patent
Giacomelli et al.

(10) Patent No.: US PP25,695 P3
(45) Date of Patent: Jul. 14, 2015

(54) RASPBERRY PLANT NAMED 'EVITA'

(50) Latin Name: ***Rubus idaeus* L.**
Varietal Denomination: Evita

(71) Applicant: SANT'ORSOLA SOCIETA' COOPERATIVA AGRICOLA (Italian Farmers Cooperative), Pergine Valsugana (IT)

(72) Inventors: Marco Giacomelli, Vigolo Vattaro (IT); Alessandra Viliotti, Vigolo Vattaro (IT); Sara Giacomelli, Vigolo Vattaro (IT); Sara Fontanari, Pergine Valsugana (IT)

(73) Assignee: SANT'ORSOLA SOCIETA' COOPERATIVA AGRICOLA, Pergine Valsugana (IT)

( * ) Notice: Subject to any disclaimer, the term of this patent is extended or adjusted under 35 U.S.C. 154(b) by 98 days.

(21) Appl. No.: 13/986,484

(22) Filed: May 7, 2013

(65) Prior Publication Data

US 2013/0305418 P1 Nov. 14, 2013

(30) Foreign Application Priority Data

May 14, 2012 (IT) ..... CPVO 20120809

(51) Int. Cl.
*A01H 5/08* (2006.01)

(52) U.S. Cl.
USPC ..... Plt./204
CPC ..... *A01H 5/0887* (2013.01)

(58) Field of Classification Search
USPC ..... Plt./204
CPC ..... A01H 5/0887; A01H 5/08
See application file for complete search history.

(56) References Cited

PUBLICATIONS

TESS retrieved on Oct. 9, 2014, retrieved from the Internet at <tmsearch.uspto.gov/bin/showfield?f=doc&state=4808:4gx9n4.3.1> 2 pp.*

* cited by examiner

*Primary Examiner* — June Hwu
(74) *Attorney, Agent, or Firm* — Ohlandt, Greeley, Ruggiero & Perle, LLP

(57) ABSTRACT

A new primocane raspberry variety named 'Evita' having good fruit colour and flavour, great and firm berries, and good tolerance to pests and diseases is disclosed.

3 Drawing Sheets

Genus and species: *Rubus idaeus* L.
Variety denomination: 'Evita'.

BACKGROUND OF THE NEW VARIETY

A new and distinct variety of red raspberry (botanically known as *Rubus idaeus* L.) hereinafter referred to by 'Evita' is disclosed. The new variety 'Evita' was obtained from the cross by seedling of individual raspberry plants of the varieties 'Dolomia' (mother parent) and 'Erika' (father parent).

The crossing for the new variety occurred in year 2007 at Vigolo Vattaro (Trento, Trentino—Italy) and it was subjected to selection in year 2009 and then tested since year 2011. The characteristics of the new variety have been found stable and have been transmitted without change through succeeding (more than 5 years) asexual propagations by root cutting.

Plant breeder's rights were applied for with the European Union on May 14, 2012. 'Evita' has not been made publicly available.

SUMMARY OF THE INVENTION

The most outstanding and distinguishing characteristics of the 'Evita' variety are hereunder reported.

Primocane raspberry plant;
Good fruit colour and flavour;
Great and firm moderate reddish orange berries;
Good tolerance to raspberry pests and diseases.

The new variety produces two crops per year and the fruits mainly ripen on current season's cane in autumn.

The new variety can be propagated by: the use of suckers produced in a spawn-bed, root cutting and use of tissue culture techniques. The root cutting is to be preferred.

BRIEF DESCRIPTION OF THE PHOTOGRAPHS

The new red raspberry variety 'Evita' is illustrated by the accompanying photographs showing typical specimens of the new variety in colour as true as reasonably possible to make the same colour illustrations of this character by conventional photographic procedures.

DETAILED DESCRIPTION

Figure 1:
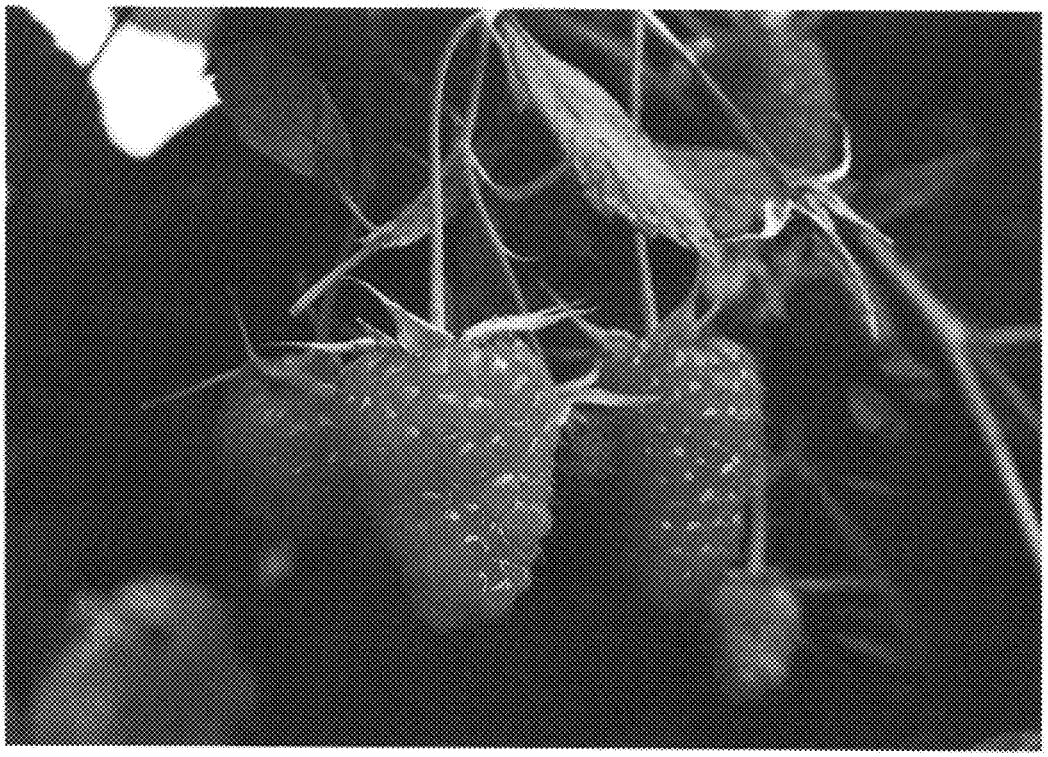
FIG. 1 is a view showing both ripe and immature fruits and leaves.
Figure 2:
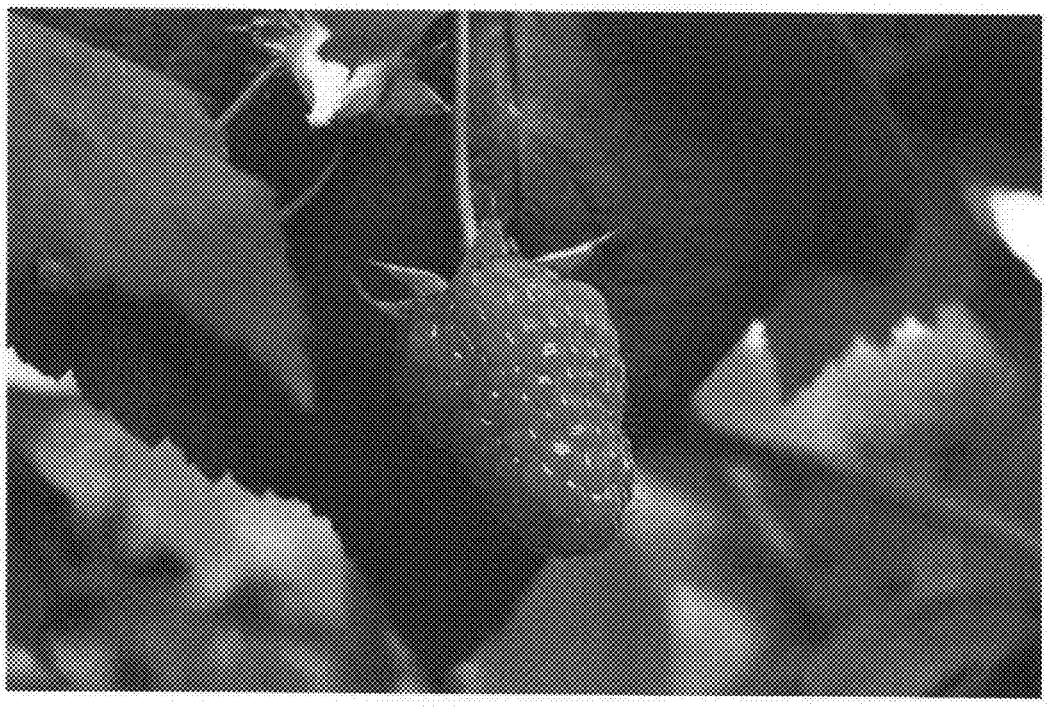
FIG. 2 is a view showing a ripe fruit size and shape and leaves.
Figure 3:
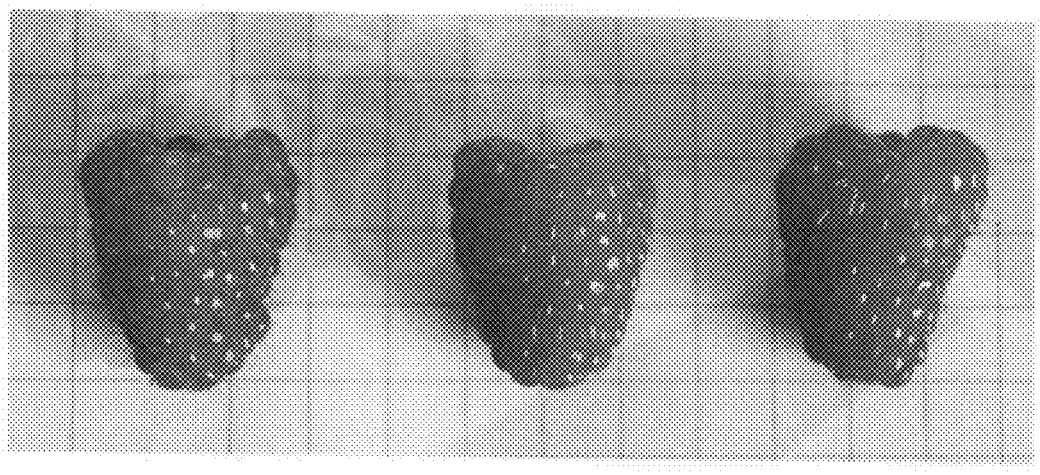
FIG. 3 is a view showing the size, shape and colour at ripening of harvested fruits.

The following detailed description sets forth the distinctive characteristics of the new variety 'Evita'. The performance of the new variety for retention of its distinctive characteristics has been evaluated through successive asexual propagations by root cutting in the Applicant's setting at Vigolo Vattaro (Trento, Trentino—Italy) under controlled conditions of temperature (minimal temperature 15° C. and maximal temperature 28° C.) in greenhouse. The growing was the out of soil type using peat as substrate.

The new variety presents a general habit with upright canes, strong vigor and a very good roots system. It is adapted to medium winter chill conditions such as those of northern Italy. Furthermore, the new variety has high productivity in autumn.

The plant assessment was performed for 3 years.

Colour references are primarily made to R.H.S. Colour Chart of The Royal Horticulutural Society of London (Edition year 2007).

Classification:

*Family*.—Rosaceae.

*Botanical*.—*Rubus idaeus* L.

*Common name*.—Raspberry.

Parentage: 'Dolomia' is the female parent and 'Erika' is the male parent.

Plant:

*Average height*.—1.78 m.

*Spread* (*average*).—0.90 m.

*Shape*.—Pyramidal.

*Vegetative bud length*.—Medium.

Primocane:

*Number of canes per plant* (*average*).—1.

*Length* (*average*).—1.78 m.

*Diameter* (*average*).—13.5 mm.

*Texture*.—Hard.

*Internode length* (*average*).—Medium to long.

*Number of fruiting laterals per cane* (*average*).—20-25.

*Number of current season's shoots*.—Few to medium (30-40 average).

*Young shoot colour*.—Strong Reddish Purple (RHS 72B).

*Dormant cane colour*.—Moderate Reddish Brown (RHS 166B).

*Fruiting cane colour*.—Light Olive Brown (RHS 199B).

Spines:

*Shape*.—Triangle.

*Size* (*average*).—Length 3.5-4 mm; Width 0.5-1 mm.

*Density* (*average*).—1.3 per cm.

*Colour*.—Dark Yellowish Pink (RHS 181D).

Foliage:

*Leaves*.—Shape: compound; odd-pinnate and subdivided in 3-5 ovate and serrate small leaves with medium rugosity; Leaf apex shape: bluntish to pointed; Leaf base shape: orbicular ovate; Upper surface colour: Strong Yellowish Green (RHS 134B); Lower surface colour: Light Yellowish Green (RHS 134D); Compound leaf average size: Length 160-200 mm; Width 130-150 mm; Lateral leaflets: touching, specular; Lateral leaflets average size: Length 130-150 mm; Width 75-85 mm; Lateral leaflets apex shape: bluntish: Lateral leaflets base shape: orbicular ovate; Lateral leaflets margin type: slightly serrated; Lateral leaflets texture: moderate hard; Terminal leaflets average size: Length 80-110 mm; Width 85-90 mm; Terminal leaflets apex shape: bluntish to pointed; Terminal leaflets base shape: orbicular ovate; Terminal leaflets margin type: slightly serrated; Terminal leaflets texture: moderate hard.

Petiole:

*Average length*.—15-20 mm.

*Surface texture*.—Hard.

Peduncle:

*Average length*.—8-14 mm.

*Surface texture*.—Hard.

Pedicel:

*Average length*.—6 mm.

*Surface texture*.—Hard.

Flowers:

*Number per plant* (*average*).—120-150.

*Length* (*average*).—14-15 mm.

*Diameter* (*average*).—14-15 mm.

*Shape*.—Racemose.

*Colour*.—Primary colour — Greenish White (RHS 155C).

*Fragrance*.—Absent.

*Blooming*.—On the current season's cane is early to medium beginning in late July and ending in early August.

Fruit:

*Predominant shape*.—Conical.

*Weight*.—6.60 g (average).

*Size*.—Ratio length:width; 2.9 cm:2.4 cm (average).

*Colour of ripe fruit*.—Moderate Reddish Orange (RHS 35B).

*Colour of immature fruit*.—From Pale Yellowish Pink (RHS 27C) to Strong Yellowish Pink (RHS 31C).

*Colour of fruit flesh*.—Strong Yellowish Pink (RHS 35C).

*Firmness*.—High.

*Drupes per fruit* (*average*).—30-40.

*Drupe size*.—Medium.

*Glossiness*.—Medium.

*Adherence to plug*.—Medium.

*Titratable acidity*.—44.62% as citric acid.

*Soluble solids*.—7.5% in Brix.

*Yield*.—1.4 Kg/plant.

*Main bearing type*.—On current year's cane from late August to late October.

*Storage capacity*.—Good shelf life.

Reproductive organs:

*Pistil number per flower* (*average*).—70-80.

*Pistil size* (*average*).—Length: 10 mm; Width: 1 mm.

*Stamen number per flower* (*average*).—70-80.

*Stamen size* (*average*).—Length: 9 mm; Width: 1 mm.

Seeds:

*Size* (*average*).—Length: 1.5-2 mm; Width: 1 mm.

*Shape*.—Elliptical.

Pest and disease resistance: 'Evita' presents strong canes resistant to pests such as *Amphorophora idaei* and diseases such as antrachnose, *botrytis*, and powdery mildew. The plants need few spray treatments for disease and pest control.

Weather resistance: The new variety is adapted to medium winter chill conditions such as in northern Italy, having, in an open-air environment, a hardiness for temperatures from −5° C. to 29° C.

COMPARISON WITH PARENTAL AND COMMERCIAL VARIETY

'Evita' differs from the parental varieties in that:

the harvest is anticipated of about 7 days respect to the parent variety 'Erika';

the crop is about 20% higher than the parent variety 'Erika';

the fruit at ripening is greater and has a more brilliant colour than the parent variety 'Dolomia'.

The similarities of new variety 'Evita' with the commercial variety 'Polka' are shown in Table 1.

TABLE 1

Comparison between 'Evita' and 'Polka'

| Characteristic | 'Evita' | 'Polka' |
|---|---|---|
| fruit color | Moderate Reddish Orange (RHS 35B) | Strong Red (RHS 41B) |
| fruit size | big | medium |

TABLE 1-continued

Comparison between 'Evita' and 'Polka'

| Characteristic | 'Evita' | 'Polka' |
|---|---|---|
| Cane color | Moderate Reddish Brown (RHS 166B) | Brownish Orange (RHS 164A) |
| plant vigor | strong | medium |

What is claimed:

1. A new and distinct variety of a primocane raspberry plant adapted to medium winter chill conditions, having good tolerance to pests and diseases, and having berries that are large, firm and conical and moderate reddish orange in colour, as substantially herein shown and described.

* * * * *